US 6,743,235 B2

United States Patent
Subba Rao

(10) Patent No.: US 6,743,235 B2
(45) Date of Patent: Jun. 1, 2004

(54) MODULAR INSTRUMENT FOR POSITIONING ACETABULAR PROSTHETIC SOCKET

(76) Inventor: Goli V. Subba Rao, 153 E. Halt Dr., Terre Haute, IN (US) 47802

( * ) Notice: Subject to any disclaimer, the term of this patent is extended or adjusted under 35 U.S.C. 154(b) by 102 days.

(21) Appl. No.: 10/271,305

(22) Filed: Oct. 15, 2002

(65) Prior Publication Data

US 2004/0073225 A1 Apr. 15, 2004

(51) Int. Cl.[7] ............................................. A61B 17/58
(52) U.S. Cl. ...................................... 606/91; 606/102
(58) Field of Search ........................... 606/90, 91, 53, 606/86, 87, 99, 102, 104

(56) References Cited

U.S. PATENT DOCUMENTS

| | | | | |
|---|---|---|---|---|
| 4,716,894 A | * | 1/1988 | Lazzeri et al. ................. | 606/91 |
| 5,284,483 A | * | 2/1994 | Johnson et al. ................ | 606/86 |
| 5,320,625 A | * | 6/1994 | Bertin ........................... | 606/91 |
| 6,214,014 B1 | * | 4/2001 | McGann ....................... | 606/102 |
| 6,383,149 B1 | * | 5/2002 | DeMayo ....................... | 600/587 |
| 6,395,005 B1 | * | 5/2002 | Lovell ........................... | 606/91 |
| 2003/0078520 A1 | * | 4/2003 | DeMayo ....................... | 600/587 |
| 2003/0153829 A1 | * | 8/2003 | Sarin et al. ................... | 600/426 |

* cited by examiner

Primary Examiner—Pedro Philogene
Assistant Examiner—David A Bonderer

(57) ABSTRACT

A modular implantation instrument for reliably positioning an acetabular prosthetic socket in the acetabulum of a pelvic bone during a total hip joint replacement surgery. The modular instrument has an interchangeable hemispherical ball member to properly engage into an acetabular prosthetic socket. A drive mechanism includes an alignment shaft member, operatively connected through an orientation pillar member to a levelling apparatus and to a laser pen apparatus. The modular instrument includes the hemipherical ball member is threadingly connected into the proximal end of said alignment shaft, the distal end of alignment shaft includes a handle and a knob. The lower end of said orientation pillar member is permanently attached to the shank of the alignment shaft member at angle of 135 degrees to the horizontal axis of said alignment shaft. The orientation pillar member includes a levelling apparatus attached to its upper end, and a laser pen apparatus attached at an intermediate location in the orientation pillar. The levelling apparatus and the laser pen apparatus are independantly adjustable parameters. Also disclosed is a detachably implantable level bit member into the levelling apparatus and a detachably implantable laser pen member into the laser pen apparatus, in order to position the acetabular prosthetic socket into correct abduction angle and antiversion angle respectively to prevent complications associated with malpositioning of an acetabular prosthetic socket.

20 Claims, 5 Drawing Sheets

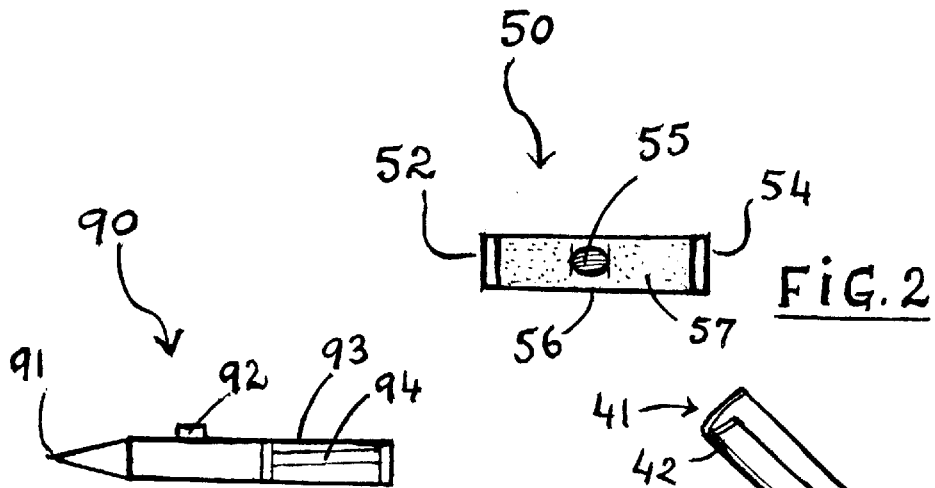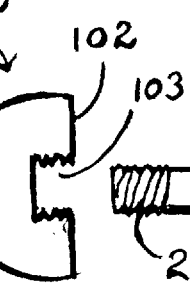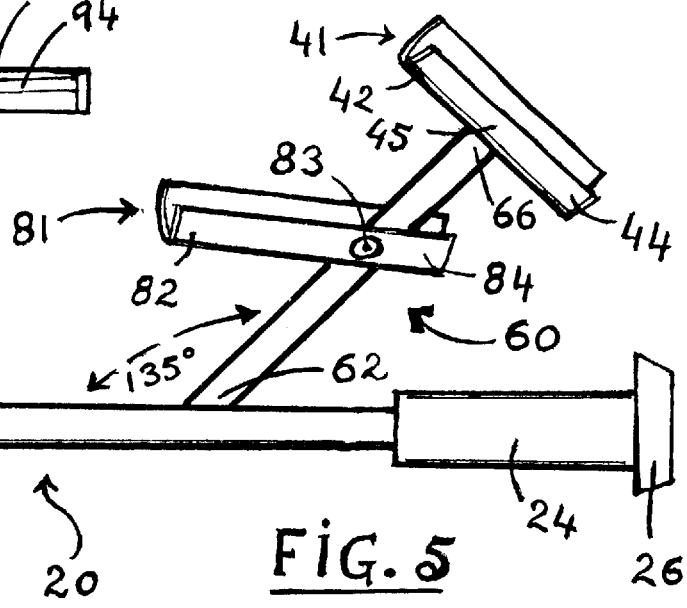

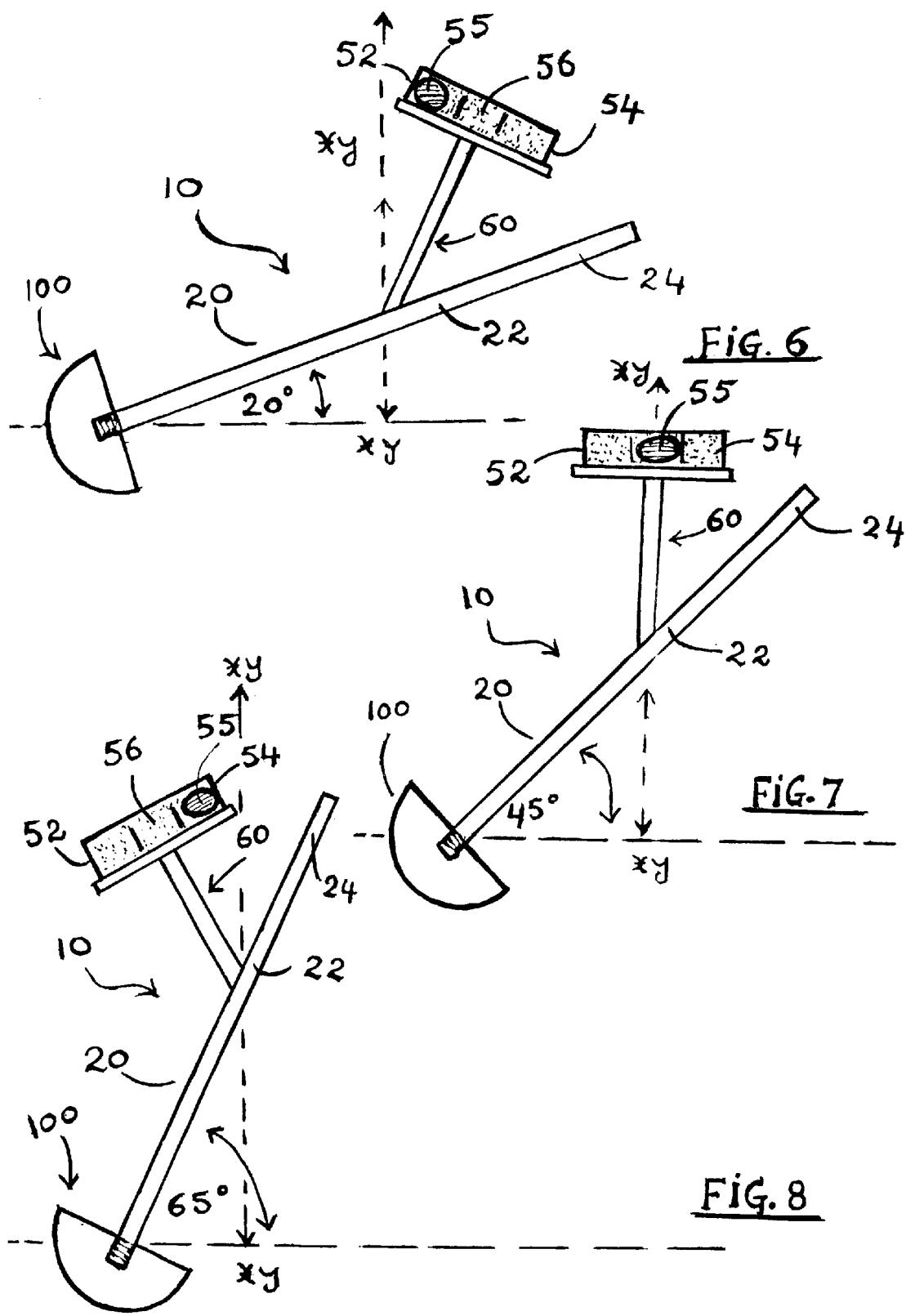

MODULAR INSTRUMENT FOR POSITIONING ACETABULAR PROSTHETIC SOCKET

BACKGROUND OF THE INVENTION

1. Field of the Invention

The present invention is related to hip joint replacement surgery and in particular for correct positioning and implantation of an acetabular prosthetic socket. The present invention provides a simple modular surgical instrument to position an acetabular prosthesis into correct position, which rely upon specific parameters and specific mechanisms incorporated into the modular instrument in order to reduce the likelihood of malpositioning an acetabular prosthetic socket into a reamed acetabulum of pelvic bone.

A malpositioned acetabular prosthetic socket can lead to several complications such as, dislocation of the hip joint, impingement of the prosthetic elements, impingement of soft tissues, decreased joint motion, painful joint, limping, increased wear and tear of the prosthetic elements, and eventual loosening and failure of the implant.

Correct anatomical placement and implantation of acetabular prosthetic socket can be surgically demanding and challenging task for orthopaedic surgeons. Correct alignment and implantation is hampered by a deep wound, bleeding from the reamed bony acetabulum, few clear reference landmarks, major neurovascular structures, close to the operating field.

To prevent malpositioning of acetabular prosthetic socket, several surgical instruments and methods have been devoloped in the art, but many such instruments are limited in application at the time of a major surgical procedure.

Hip joint replacement surgery requires knowledge of topographical and surgical anatomy of patients and clinical pathology of the hip joint. Many currently available acetabular prosthetic socket alignment apparatus and methods, merely rely upon reference landmarks external to the pelvis of a patient, the reliance placed on such external landmarks on pelvis tend to introduce inadvertent misjudgements arising from the variations in patient's external landmarks associated with obesity, patient's position on the operating table, previous surgeries on the hip or pelvis, and surgeon's proprioceptive skills, and the results can vary widely, wherein reliable and consistant results are not assured.

Instruments incorporating electronics, computer tomographic scans, intraoperative radiological monitoring, have been used to position an acetabular prosthetic socketc correctly, but then these instruments and methods can be expensive, complicated, invasive, again some of them can be misleading and are not widely practical, and are not widely popular.

2. Description of the Related Art

The following patents are related for positioning and implanting an acetabular prosthetic cup into acetabulum of a pelvic bone.

U.S. Pat. No. 4,305,394 to Bertuch Jr. (1981)
U.S. Pat. No. 4,475,549 to Oh (1984)
U.S. Pat. No. 4,994,064 to Aboczsky (1991)
U.S. Pat. No. 5,037,424 to Aboczsky (1991)
U.S. Pat. No. 4,141,512 to Farmer et al (1992)
U.S. Pat. No. 5,284,483 to Johnson (1994)
U.S. Pat. No. 5,320,625 to Bertin (1994)
U.S. Pat. No. 5,364,403 to Petersen (1994)
U.S. Pat. No. 5,540,697 to Rehmann (1996)
U.S. Pat. No. 4,716,894 to Lazzari (1998)
U.S. Pat. No. 6,214,014 BI to McGann (2001)
U.S. Pat. No. 6,395,005 BI to Lovell (2002)

For example U.S Pat. No. 4,305,394 to Bertuch Jr. discloses an acetabular prosthetic socket positioning instrument that has an interchangeable ball and a flange and a drive mechanism operatively connected through a drive coupling rod, flexible drive cable and drive member and carrying such ball. The instrument also discloses a left hand handle, a stabilising rod, a right hand handle and a L shaped hollow drive housing. Similarly, U.S. Pat. No. 475,549 to Indong Oh discloses an acetabular cup positioner, comprising a head having an axis which is receivable in the acetabular cup, a first arm coupled to the head and extending from the head at an acute angle, and a second arm coupled to the first arm at a location spaced from the head and the arms and the axis are coupled the first arm such that the antiversion angle can be established for the right and left hips by aligning the first and second hands, respectively with the patient axis.

U.S. Pat. No. 4,716,894 to Lazzeri et al; discloses an acetabular cup inserting instrument comprising a first handle and a second handle extending therefrom, the second handle is selectively locable in a desired position with respect to the first handle.

Instruments that address the orientation, inserting and impacting problems for acetabular prosthetic sockets are known in the art. For example U.S. Pat. No. 4,994,064 and U.S. Pat. No. 5,037,424 to Robert Aboczky discloses an instrument comprising an impaction rod, coupling rod, pivoting rod and supporting rod. Acetabular prosthetic cup is aligned and inserted in accordance with a plane normal to line between the right and left anterior iliac spines. The alignment arrangement includes a bar which is rotatably adjustable about the axis of coupling rod, and which is aligned normal to a line which crosses from posterior superior iliac to the anterior iliac spine. U.S. Pat. No. 5,141,512 to Malcom Fraser et al; discloses a modular apparatus for proper alignment of an acetabular prosthetic socket, includes a frame having feet which are placed against anterior iliac spines and symphysis pubis. The invention includes a light beam directed from a source through an aperture to a mirror mounted on an inserter. The light beam is reflected back from the mirror to a target region. When the incident and reflected beam are coincident the cup is aligned for correct placement. The target region is rotatably and pivotably mounted for precise adjustments of the angle of abduction and antiversion respectively. The instrument appear bulky, complicated and occupy considerable space at the time of surgery, and also appear not suitable for patients placed in lateral position.

U.S. Pat. No. 5,284,483 to Erin Johnson discloses an instrument comprising a first elongated handle, a second elongated handle extending therefrom. The second handle is capable of ratcheting about the longitudinal axis of the first elongated handle. The second handle may be selectively locked in a desired position with respect to the first handle by means of a control on the ratchet mechanism to aid proper positioning an acetabular prosthetic cup. Similarly U.S. Pat. No. 5,320,625 to Kim Bertin discloses an apparatus that includes a orientation bar and an alignment arm, laterally displaced from the longitudinal axis of the apparatus and selectively fixed or rotatably connected in order to implant the acetabular prosthetic cup in desired orientation.

Similarly U.S. Pat. No. 5,364,403 to Thomas Petersen discloses an instrument, provides a resilient collar at one end connecting the acetabular cup, a sighting guide and an A-shaped alignment guide to check the alignment of the acetabular cup with anatomical check points on the patient. Similarly apparatus U.S. Pat. No. 5,540,697 to Mark Rehmann discloses both axial and angular alignment references to fecilitate correct alignment of an acetabular prosthetic cup, the alignment includes an abduction indicating member and antiversion indicating member connected to an elongated tool body to provide an axial alignment guide.

U.S. Pat. No. 6,214,014 BI to William McGann discloses an alignment system for hip replacement surgery, the acetabular guide comprises of three components, the laser pointer, goniometer, and a swing arm. The swing arm includes a window with an alignment guide, the laser light is directed towards a wall in the operating room and a mark is made on the wall where the laser light points. The goniometer and the laser pointer are removed after appropriate mark is imdicated on the operating room wall. The acetabular cup is inserted with the aid of a handle and the handle is appropriately aligned by inserting the laser pointer into the bore and moving the handle until the laser light of the pointer is aligned with the previously indicated mark on the wall, and once this has occured the acetabular cup is finally inserted into the predetermined position. Again such system utilises a goniometer and laser light nonspecifically laser light pointing on to a wall, and is undesirably limited in application due to, for example variations associated with positioning of the patient on the operating table, shape of the wall, size of the wall, position of the operating table and other variables in the operating room at the time of surgery.

Similarly alignment methods and apparatuses that utilize natural landmarks available on pelvic bones to guide the alignment of an acetabular device in connection with the implant of a prosthetic hip joint at an implant site in the pelvis are known in the art. For example U.S. Pat. No. 6,395,005 BI to Timmothy Lovell discloses an acetabular alignment apparatus and method, the device includes a positioning shaft having a longitudinal axis and locators are mounted upon the positioning shaft for placement adjacent sellected landmarks on the pelvis to orient the shaft axis of a prepared acetabulum at the implant site in order to place the shaft axis at a prescribed angle of abduction and prescribed angle of antiversion thereby orienting the acetabular device at the appropriate angle of abduction and appropriate angle of antiversion.

Similarly the current positioning instruments to implant an acetabular prosthetic sockets mostly rely upon non-specific parameters such as: external reference landmarks on the patient, non-specific alignment bars, rods, shafts, pins, bolts and nuts, complicated attachments, direct observation of the prosthetic cup by the surgeon at the time of surgery, complicated ways of utilising laser beam, and time consuming parameters.

What is needed is an improved modular instrument to correctly position an acetabular prosthetic socket, wherein the instrument is simple to understand, simple to assemble, simple to use more accurately with precision, wherein the surgeon utilises the instrument faster with confidence at the time of surgery.

What is also needed a modular instrument that also provide a levelling apparatus and a laser beam apparatus, desirable mathematical accuracy, that rely on specific dependable parameters.

SUMMARY OF THE INVENTION

The object of the present invention is to provide an acetabular prosthetic socket positioning instrument, an improved modular surgical instrument for correct positioning of the prosthetic socket in a reamed bony acetabulum of a patient, during a total hip joint replacement surgical procedure. The present invention provides a simple modular instrument, easy to assemble, easy to understand and versatile in application. The present invention provides an improved and reliable modular instrument which can be used to establish the correct abduction and antiversion angles of the acetabular prosthetic socket, by aligning the alignment shaft, the orientation pillar, the levelling apparatus and the laser pen apparatus.

In one form thereof, the present invention provides a hemispherical ball member, adapted to cooperate with an acetabular prosthetic socket and an alignment shaft having an intermediate shank, a distal handle and an impaction knob. The lower end of an orientation pillar is coupled and anchored into the shank of the alignment shaft at an oblique angle of 135 degrees. The upper end of orientation pillar is incorporated with a levelling apparatus, and the intermediate part of orientation pillar is incorporated with a laser pen apparatus.

In preffered form, the proximal end of the modular instrument comprises of hemispherical ball member having an outer convex surface adapted to cooperate with the acetabular socket. In a preffered form of the invention, the inner flat surface of the hemispherical ball member further comprises of a threaded pit disposed in the center of the flat surface. More preferably, the proximal end of the alignment shaft is adapted to have threaded means, and the connection between the hemispherical ball member and the alignment shaft is through a threading mechanism.

More preferably, the hemispherical ball member is detachably attached to the proximal end of the alignment shaft by means of corresponding threads.

In a preffered form, the modular acetabular prosthetic socket positioning instrument further comprises of a levelling apparatus incorporated into the upper end of orientation pillar, is to establish correct abduction angle of the acetabular prosthetic socket in the acetabulum.

In a preffered form, the modular instrument further comprises of a laser pen apparatus, incorporated at an intermediate location in the orientation pillar, is to establish correct antiversion and retroversion angles of the acetabular prosthetic socket in the acetabulum.

In another form thereof, the present invention provides a modular instrument for custom fitting an acetabular prosthetic socket to individual patient, in this method the hemispherical ball member is sellected from a plurality of different hemispherical ball members, depending on the inner size of an acetabular prosthetic socket to be implanted into the reamed bony acetabulum.

In a preffered form of the invention, the orientation pillar member is coupled and anchored to the alignment shaft at an oblique angle of 135 degrees at an intermediate location in the shank, to the horizontal axis of the alignment shaft.

In one form thereof, the orientation pillar comprises of a levelling apparatus incorporated at its distal end. The levelling apparatus further consists of a semitubular bar member and a tubular level bit. The level bit member is detachably installed into the semitubular bar member, with click-in and click-out method.

In another form thereof, the present invention also provides a laser pen apparatus for custom fitting a prosthetic socket in desired position of antiversion or retroversion as the case may require. In this laser pen apparatus, a semitubular arm member is coupled to the orientation pillar member with -a hinge mechanism. A laser pen is detachably installed into the semitubular arm member so that the laser beam directed towards the hemispherical ball member. The hinge mechanism of the semitubular arm member permit up and down movement of semitubular arm member and the laser pen and to focus the laser beam on to the patient's predetermined anatomical landmarks on the boney pelvis.

In a preffered form of the present invention, the semitubular bar member is permanently attached at the center of its convex surface, equal length on either side, to the center of the distal end of orientation pillar, means, the semitubular member is placed perpendicular to the longitudinal axis of orientation pillar.

In a preffered form of the present invention, the air bubble in the level bit cooperate with the semitubular bar, with the orientation pillar and the alignment shaft to position and implant acetabular prosthetic socket into correct abduction angle of 45 degrees or desired anatomical position in the reamed acetabulum.

One advantage of the present invention is easy to assemble the hemispherical ball member into the alignment shaft, to cooperate with the acetabular prosthetic socket to be implanted into the patient's acetabulum.

One advantage of the present invention is easy to assemble the level bit into the semitubular bar member of the levelling apparatus.

Yet another advantage of the present invention is easy to assemble the laser pen into the semitubular arm member of the laser pen apparatus Yet another advantage of the present invention is easy to manoeuver the modular instrument to correctly position an acetabular prosthetic socket, by using the hemispherical ball member, the alignment shaft member, and the orientation pillar by utilising the more accurate methods of assessment incorporated into the levelling apparatus and into the laser pen apparatus.

Yet another advantage of the present invention is simple and easy application and saves much needed time for the surgeon at the time of surgery.

Yet another advantage of the present invention is provide confidence to the surgeon and the training staff for correct implantation of an acetabular prosthetic socket during hip joint replacement surgery.

While pre-operative imaging techniques and intra-operative imaging techniques and complicated instruments can be used to determine the abduction angle, antiversion angle, adduction angle, retroversion angle of a particular patients acetabulum, such techniques are often only an approximation, and are difficult to interpret during the actual surgical procedure in the operating room, wherein the surgical wound is deep, where the reamed acetabulum is oozing blood and obscures the acetabulum, wherein the operating time is constrained due to old age of the patients, and also where the normal anatomy of the patient is distorted due to advanced asteoarthritis or other pathological process and also where the neurovascular structures are close to the operating field.

The present invention provides the necessary adjustments in various angles of abduction, adduction, antiversion, and retroversion, at the time of a major hip joint replacement surgical procedure. The inventive modular instrument can prevent several intra-operative and post-operative complications associated with malpositioning of an acetabular prosthetic socket.

BRIEF DESCRIPTION OF DRAWINGS

The above-mentioned and other features and advantages of this invention, and manner of attaining them, will become more apparent and the invention will be better understood by reference to the following description of embodiments of the invention taken in conjunction with the accompanying drawings, wherein:

FIG. 2 is side sectional view of the level bit member.

FIG. 3 is a sectional view of the laser pen member.

FIG. 4 is a sectional view of the hemispherical ball member.

FIG. 5 is a fragmentary sectional view illustrating the alignment shaft member incorporating the orientation pillar member at an oblique angle of 135 degrees. Orientation pillar member includes, sectional view of semitubular bar member and semitubular arm member to accommodate the level bit member and laser pen member respectively FIG. 6 is a sectional view illustrating the level bit member incorporating the present invention, wherein the air bubble migrating towards proximal end of level bit.

FIG. 7 is a sectional view illustrating the level bit member incorporating the present invention, wherein the air bubble migrating towards the center of level bit. The orientation pillar member standing vertical.

FIG. 8 is a sectional view illustrating the level bit member incorporating the present invention, wherein the air bubble migrating towards the distal end of level bit.

Corresponding reference charectors indicate corresponding parts throughout the several views. The exemplification set forth herein illustrates preffered embodiments of the invention, in several forms, and such exemplifications are not be constructed al limiting the scope of the invention in any manner.

DETAILED DESCRIPTION OF THE PREFERRED EMBODIMENTS

Figure 1:
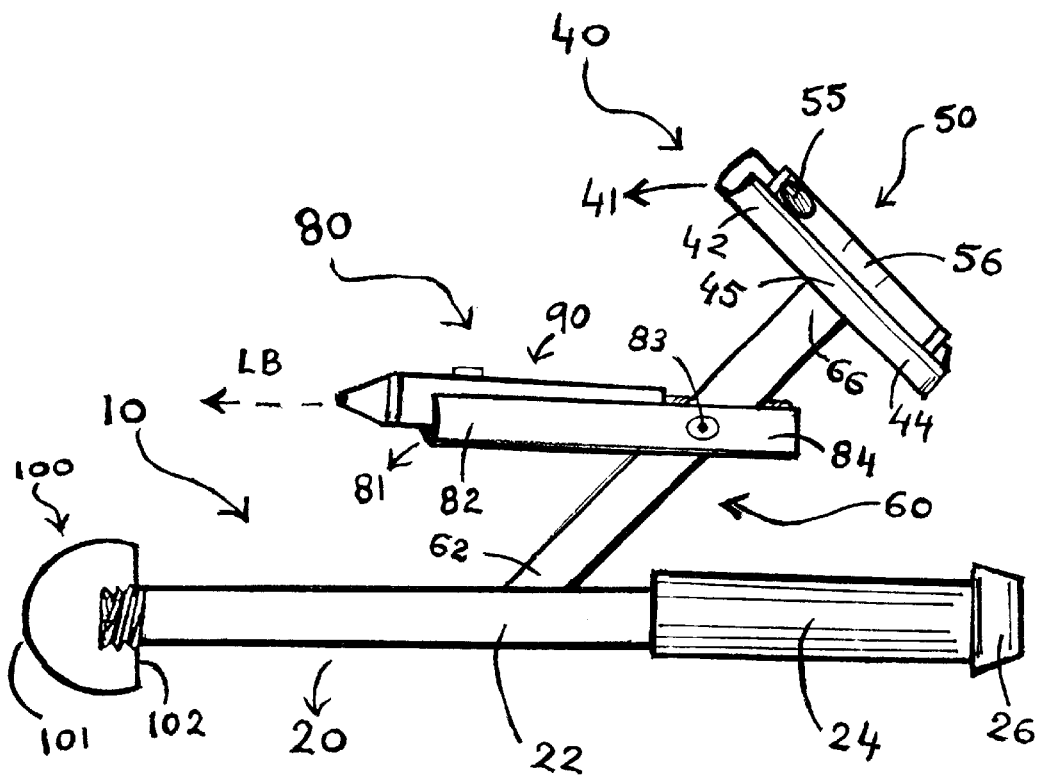
FIG. 1 is an exploded side sectional view of a modular instrument for positioning an acetabular prosthetic socket incorporating the present invention.

Referring now to the drawing, and especially to FIG. 1 thereof, illustrates a particularly advantageous embodiment of a modular acetabular prosthetic socket positioning instrument 10, in the form of a hemispherical ball member 100, an alignment shaft member 20, includes a shank 20, a handle 24, and a knob 26, incorporated into the alignment shaft shank 22, is an orientation pillar 60.

FIG. 1 shows an acetabular prosthetic socket inserting instrument 10, includes a hemispherical ball member 100, having an outer convex surface 101 to engage cooperatively with an acetabular prosthetic socket 200 as is known in the art.

With reference to FIGS. 1 and 4, the hemispherical ball member 100 is provided with an inner flat surface 102, a central threaded pit 103 includes a means for threadingly engaging into the proximal end 22 of alignment shaft 20. The alignment shaft 20 includes a distal handle 24 and an impaction knob 26 to securely hold and properly position and implant an acetabular prosthesis 200 into correct position. The lower end 62 of orientation pillar 60 is coupled and anchored obliquely at an angle of 135 degrees with the shank 22 of alignment shaft 20 at a predetermined location incorporating the present invention.

With reference to FIGS. 1–10, orientation pillar 60 in a preferred embodiment composed of two apparatuses. A levelling apparatus 40 and a laser pen apparatus 80, wherein both apparatus function independently. The levelling apparatus 40 includes a semitubular bar member 41 which is anchored perpendicularly at the distal end of 66 of orientation pillar 60.

As shown in FIG. 5 the semitubular bar member 41 consists of a proximal end 42, a center 45 and a distal end 44. The semitubular bar member 41 is securely anchored at the center 45 of its convex surface to the distal end 66 of orientation pillar member 60, means the semitubular bar member is perpendicular to the long axis of orientation pillar member 60 and equal length on either side of distal end of orientation pillar member 66.

With reference to FIG. 2 level bit member 50 is a tubular structure made up of tranparent shell, sealed on both proximal end 52 and distal end 54. The level bit contains fluid 57 and an air bubble 55. The level bit member 50 is of equal length and diameter to that of semitubular bar member 41. It can be easily appreciated that the level bit member 50 is removably installed into the the shallow concave surface of the semitubular member 41 by click-in and click-out method for easy installation and removal, to help sterilisation and replacement purpose. Thus the semitubular bar member 41 provides flexibility of accommodating a level bit member 50 of same length, diameter and circumference.

When the air buuble 55 migrates to the center 56 of level bit 50, the semitubular bar 41 and the level bit 50 therein becomes horizontal and becomes parallel to the horizontal axis of the patient. Such maneuver in the levelling apparatus 40, draws the orientation pillar 60 into a vertical axis to the horizontal axis of patient, and such maneuver draws the alignment shaft 20 into 45 degrees of abduction in order to position an acetabular prothetic socket 200 into correct abduction angle of 45 degrees at the time of surgery.

FIGS. 6–8 illustrates the level bit member 50 the semitubular bar member 41 and the orientation pillar 60, and are designed to indicate the abduction angle of alignment shaft member 20, during positioning of an acetabular prosthetic socket 200. It can be appreciated, since the lower end 62 of orientation pillar 60 is anchored to the alignment shaft shank 22 at an oblique angle of 135 degrees, since the levelling apparatus 40 is fixed at a perpendicular plane to the long axis of orientation pillar 60, any variations in the levelling apparatus 40 are imparted, through the orientation pillar 60 into the abduction angle of alignment shaft 20 and vice-versa.

It can be appreciated as shown in FIG. 7, therefore, when acetabular prosthetic socket 200 is correctly positioned, the alignment shaft 20 is abducted to an abduction angle of 45 degrees wherein the orientation pillar 60 becomes perpendicular to the floor of operating room or to the horizontal axis of patient. The semitubular bar 41 and the level bit 50 becomes parallel to the operating room floor or to the horizontal axis of patient, and the air bubble 55 migrates to the center of level bit 50.

With reference to FIGS. 6–8 the advantages of present invention is that the extent the sensitive index of air bubble member 55, in the levelling apparatus 40 cooperate with orientation pillar 60 in order to align the alignment shaft 20 to position acetabular prosthetic socket into correct angle of abduction.

It can also be appreciated the present invention utilises sensitive indexes and multiple adjustable parameters and avoids the errors associated with other inventions known in the art.

FIGS. 6–8 show abduction angle variations of alignment shaft 20 and the relative variations in the axis of orientation pillar 60 and the levelling apparatus 40.

FIG. 6, illustrates various sensitive indexes of the modular instrument 10 wherein, when the abduction angle of alignment shaff 20 is less than 45 degrees, the orientation pillar 60 inclines to the right side of known perpendicular or vertical axis XY. The proximal end 42 semitubular bar member 41 inclines upward position and the distal end 44 inclines to a downward position, wherein the air bubble 55 migrates to the proximal end 52 of level bit 50.

FIG. 8, illustrates various sensitive indexes of the modular instrument 10, wherein, when the abduction angle of alignment shaft 20 is more than 45 degrees, the orientation pillar 60 inclines to the left side of known perpendicular or vertical axis XY. The proximal end 42 of semitubular bar member 41 inclines downward position and the distal end 44 inclines to upward position, wherein the air bubble 55 migrates to the distal end 54 of level bit 50.

It can be appreciated that the present invention avoids errors known in the art, such a naked eye measurements or other nonspecific judgements to position an acetabular prosthetic cup into acetabulum. Another advantage of present invention is, multiple sensitive parameters and indexes are used to position an acetabular prosthetic into correct position. Further it is possible with the present invention to adjust the abduction angle of alignment shaft to any desired correct abduction angle at the time of surgery which might be desirable in a reamed acetabulum, when pre-operative data used to establish acetabular angle are inaccurate.

Figure 9:
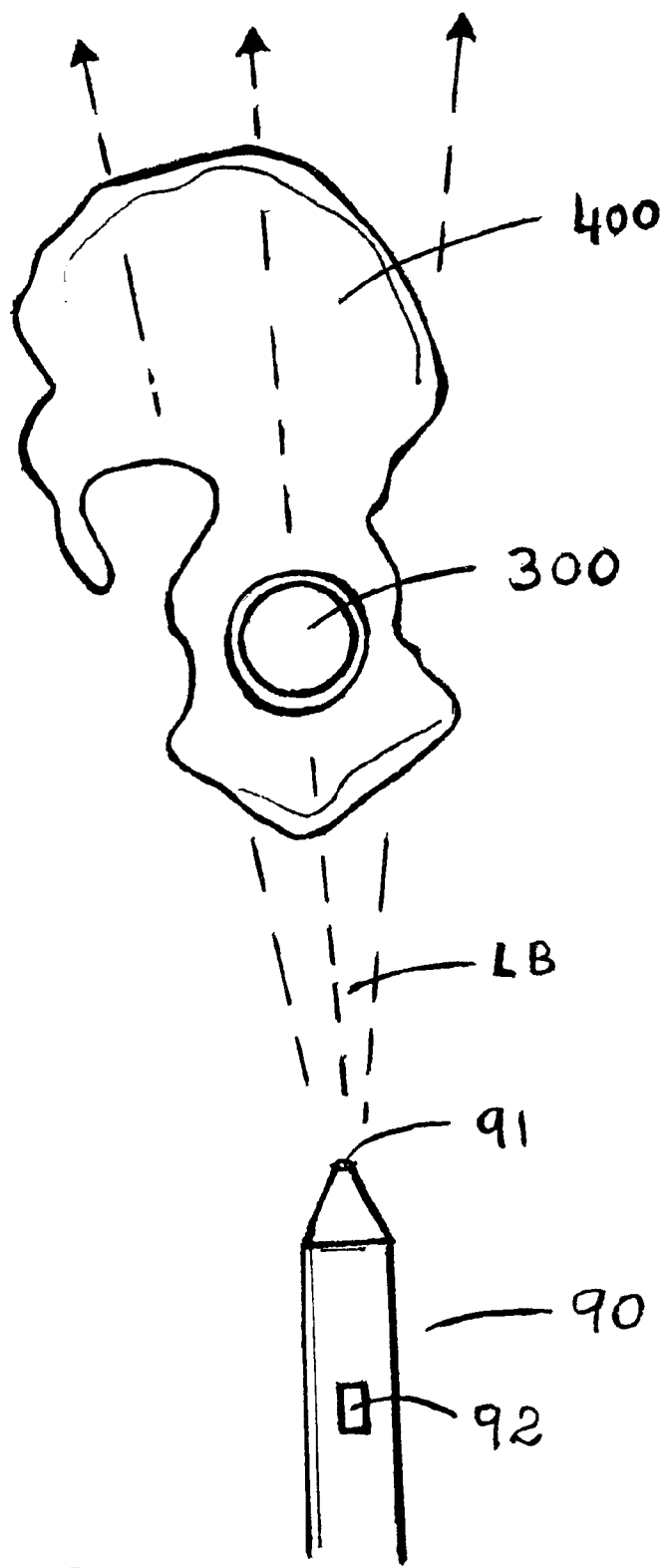
FIG. 9 is a plan view illustrating part of laser pen member, laser beams and side of pelvis for antiversion and retroversion angle adjustments
Figure 10:
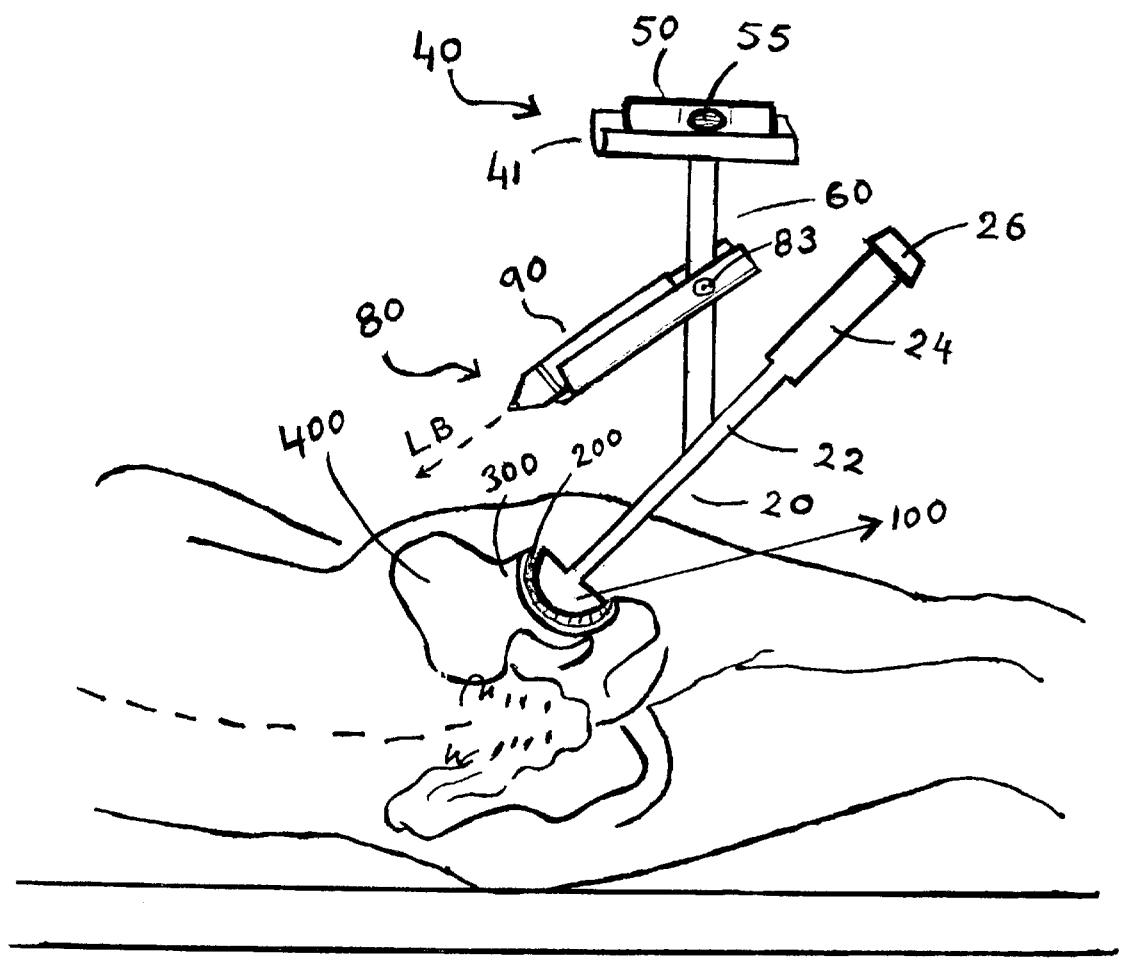
FIG. 10 is an elivational side view of the present modular instrument illustrating coorrect positioning of an acetabular prosthetic socket in acetabulum of pelvis. The patient is in lateral position.

With reference to FIG. 9, one of the advantages of the present modular instrument 10 is the incorporation of laser pen apparatus for correct positioning of an acetabular prosthetic socket in desired antiversion or retroversion angle at the time of surgery using a laser beam LB. As shown in FIG. 5 a semitubular arm member 81 consists of a proximal end 82 and a distal end 84. As shown in FIGS. 1 and 5, the orientation pillar 60 is coupled with the distal part 84 of semitubular arm member 81, at an intermediate location 64 of orientation pillar 60, with an adjustable hinge mechanism 83, wherein the proximal end 82 of semitubular arm member 81 faces towards the hemispherical ball member 100, and the distal end 84 faces towards the handle 24 of alignment shaft 20.

The next component of laser pen apparatus 80, as shown in FIG. 3 includes a laser pen 90 which consists of a proximal end with an aperture 91 for emmission of a laser beam LB, includes a a switch 92 and a battery compartment 93 to accommodate a battery 94. It can be appreciated the laser pen member 90 is detachably installed into semitubular arm member 81 by means of click-in and click-out method for easy installation and easy removal for sterilisation or replacement purpose or replacement of battery.

With reference to FIGS. 6–9, it can be appreciated that the laser pen apparatus 80 is an independant parameter, adjustable in nature for correct angle of antiversion or retroversion to position an acetabular prosthetic socket 200. Thus the hinge mechanism 83 at orientation pillar 64 provides flexibility of above-down and side to side movement of proximal end 82 of semitubular arm member 81. As shown in FIG. 9, with the present invention it is made possible to direct laser beam LB, over acetabulum 200 or pelvis 400 for desirable adjustments in the angle of antiversion or retroversion for correct positioning of acetabular prosthetic socket at the time of surgery.

The above described preffered embodiments are intended to illustrate the principles of the invention, but not to limit the scope of the invention. While this invention has been described as having an exemplary design, the present invention may be further modified within the spirit and scope of this disclosure. This application is therefore intended to cover any variations, uses or adaptations of the invention using its general principles. Further this application is intended to cover such departures from present disclosure as come within known or customary practice in the art to which the invention pertains.

What I claim as my invention is:

1. A modular instrument for correct positioning of an acetabular prosthetic socket comprising;
    a hemispherical ball member having a threaded pit in the center of its's flat surface;
    an alignment shaft having a threaded proximal end;
    an orientation pillar incorporated with a levelling apparatus fixed at it's top end, and a laser pen apparatus coupled at an intermediate location in the orientation pillar.

2. A modular instrument as defined in claim 1, wherein the hemispherical ball member comprises an outer convex non-slip surface adapted to cooperate with an acetabular prosthetic socket a means for reliably engaging and releasing the said socket during the implantation into reamed bony acetabulum.

3. A modular instrument as defined in claim 2, wherein said hemispherical ball member comprises of a threaded pit in the central axis of it's flat inner surface, and a threaded connector at the proximal end of the alignment shaft member, wherein the said hemispherical ball member and said alignment shaft are threadingly connected.

4. A modular instrument as defined in claim 3, wherein said hemispherical ball member and said alignment shaft are detachably attached, wherein different size hemispherical ball member can be sellected from a plurality of different size hemispherical ball members for custom fitting the prosthetic socket into the reamed bony acetabulum.

5. A modular instrument as defined in claim 2, wherein the convex surface of the hemispherical ball member is made up of slip resistant surface, made to adapt and cooperate with the concave surface of an acetabular proshetic socket.

6. A modular instrument as defined in claim 1, wherein the alignment shaft member includes an intermediate shank for securely attaching an orientation pillar at an angle of 135 degrees.

7. A modular instrument as defined in 1, includes an orientation pillar member consisting of a lower end, an intermediate part and an upper end.

8. A modular instrument as defined in claim 7, wherein the lower end of orientation pillar is permanently attached to the shank of alignment shaft at an oblique angle of 135 degrees to the horizontal axis of said alignment shaft.

9. A modular instrument as defined in claim 8, wherein the orientation pillar member further comprises of a levelling apparatus incorporated into its upper end.

10. A modular instrument as defined in claim 9, wherein the upper end of orientation pillar is permanently attached with a semitubular bar member, generally disposed perpendicularly to the vertical axis of the orientation pillar member, and of equal length on either side of the said vertical axis.

11. A modular instrument as defined in claim 9, wherein a level bit member is detachably installed into the semitubular bar member of levelling apparatus to establish the vertical axis of orientation pillar relative to patient's horizontal axis, and to establish the abduction angle of alignment shaft member relative to patient's horizontal axis.

12. A modular instrument as defined in claim 11, wherein the level bit member is installed into the semitubular member by click-in method; and
    said level bit member further includes an air bubble in a liquid medium, wherein the air bubble migrates to the center of the level bit when the alignment shaft member is abducted to 45 degrees of abduction to the horizontal axis of patient.

13. A modular instrument as defined in claim 12, wherein said air bubble in the level bit member migrates to the proximal end of the said level bit, when the alignment shaft is abducted less than 45 degrees of abduction to the horizontal axis of patient.

14. A modular instrument as defined in claim 12, wherein said levelling apparatus, said orientation orientation pillar member, and said alignment shaft member being used in cooperation to correctly position an acetabular prosthetic cup at a predetermined angle of abduction and antiversion or retroversion.

15. A modular instrument as defined in claim 11, wherein said air bubble in the level bit member migrates to the distal end of the said level bit, when the alignment shaft is abducted more than 45 degrees of abduction to the horizontal axis of patient.

16. A modular instrument as defined in claim 11, wherein said level bit member is detachably installed into the said semitubular bar member, by means of click-in and click-out method for easy installation, for easy replacement, for sterilisation and for reducing the costs.

17. A modular instrument as defined in claim 1, wherein the implant instrument further includes a laser pen apparatus, wherein a laser pen being installed into a semitubular arm member by a click-in method.

18. A modular instrument as defined in claim 17, wherein the said semitubular arm member is attached to the orientation pillar member at an intermediate location, wherein the distal part of said semitubular member is coupled with a hinge mechanism, wherein the said laser pen angle can be adjusted during the step of implanting an acetabular prosthetic cup for correct angle of antiversion or retroversion.

19. A modular instrument as defined in claim 17, wherein the laser pen member is detachably installed into the semitubular arm member by click-in and click-out method for easy installation, for easy replacement, for sterilisation and for safety purpose.

20. A modular instrument as defined in claim 1, wherein a hemispherical ball member is threadingly connected to an alignment shaft member, wherein the alignment shaft member is housed with an orientation pillar member, and the orientation pillar member is incorporated with a levelling apparatus and a laser pen apparatus further comprising:
    adjustments in hemispherical ball member causes corresponding adjustments in the alignment shaft; and vice versa;
    adjustments in the alignment shaft member causes corresponding adjustments in the orientation pillar member,
    adjustments in the orientation pillar member causes corresponding adjustments in the levelling apparatus and laser pen apparatus and vice versa.

* * * * *